(12) United States Patent
Rodriguez et al.

(10) Patent No.: US 8,784,844 B2
(45) Date of Patent: Jul. 22, 2014

(54) ARABINOGALACTAN FOR ENHANCING THE ADAPTIVE IMMUNE RESPONSE

(75) Inventors: Bryan Rodriguez, San Antonio, TX (US); Kevin Q. Owen, Canyon, TX (US); Ulla Freitas, Lörrach (DE); Jay Udani, Agoura Hills, CA (US)

(73) Assignee: Lonza Ltd., Basel (CH)

( * ) Notice: Subject to any disclaimer, the term of this patent is extended or adjusted under 35 U.S.C. 154(b) by 194 days.

(21) Appl. No.: 12/894,266

(22) Filed: Sep. 30, 2010

(65) Prior Publication Data

US 2011/0076306 A1    Mar. 31, 2011

Related U.S. Application Data

(60) Provisional application No. 61/247,204, filed on Sep. 30, 2009.

(51) Int. Cl.
*A61K 31/70*    (2006.01)

(52) U.S. Cl.
USPC ...................................................... 424/278.1

(58) Field of Classification Search
None
See application file for complete search history.

(56) References Cited

U.S. PATENT DOCUMENTS 5,756,098 A     5/1998  Price et al.
6,303,584 B1 *  10/2001 Richards .......................... 514/54

FOREIGN PATENT DOCUMENTS

EP          0086608       8/1983

OTHER PUBLICATIONS

Talkington et al. (Microb. Path., 21:17/22, 1996).*
Crick et al. (Glycobiol., 11:107R-118R, 2001).*
Artz et al., "Pneumococcal Vaccination and Revaccination of Older Adults", Clinical Microbiology Reviews, vol. 16, No. 2, pp. 308-318; 2003.
Classen et al., "Characterization of an Arabinogalactan-Protein Isolated from Pressed Juice of *Echinacea purpurea* by Precipitation with the Beta-glucosyl Yariv Reacent", Carbohydrate Research, vol. 327, pp. 497-504; 2000.
Currier et al., "Effect Over Time of In-Vivo Administration of the Polysaccharide Arabinogalactan on Immune and Hemopoietic Cell Lineages in Murine Spleen and Bone Marrow", Phytomedicine, vol. 10, pp. 145-153; 2003.
Deloria-Knoll et al., "Effect of Zinc and Vitamin A Supplementation on Antibody Responses to a Pneumococcal Conjugate Vaccine in HIV-positive Injection Drug Users: A Randomized Trial", Vaccine, vol. 24, pp. 1670-1679; 2006.
Kelly, "Larch Arabinogalactan: Clinical Relevance of a Novel Immune-Enhancing Polysacharide", Alternative Medicine Review, vol. 4, pp. 96-103; 1999.
Lamm et al., "Persistent Response to Pneumococcal Vaccine in Individuals Supplemented with a Novel Water Soluble Extract of *Uncaria tomentosa*, C-Med-100", Phytomedicine, vol. 8, pp. 267-274; 2001.
Moriguti et al., "Effects of Arginine Supplementation on the Humoral and Innate Immune Response of Older People", European Journal of Clinical Nutrition, vol. 59, pp. 1362-1366; 2005.
Roxas et al., "Colds and Influenza: A Review of Diagnosis and Conventional, Botanical, and Nutritional Considerations", Alternative Medicine Review, vol. 12, No. 1, pp. 25-48; 2007.
Larex, Inc., GRAS Notice for Arabinogalactan from the Eastern Larch Tree, pp. 1-327, 2001; and U.S. Food and Drug Administration Agency Response Letter GRAS Notice No. GRN 000084, pp. 1-2; 2002.

* cited by examiner

*Primary Examiner* — Brian J Gangle
(74) *Attorney, Agent, or Firm* — Hoffmann & Baron, LLP

(57) ABSTRACT

The present invention discloses a composition containing Arabinogalactan for enhancing the adaptive immune response in subjects to foreign antigen(s) by administering said composition prior, during and after the phase of exposure to said foreign antigen(s). Furthermore, the present invention relates to a vaccination kit comprising a composition comprising Arabinogalactan and a vaccine.

5 Claims, No Drawings

ARABINOGALACTAN FOR ENHANCING THE ADAPTIVE IMMUNE RESPONSE

CROSS-REFERENCE TO RELATED APPLICATION

This application claims the benefit of priority from U.S. Provisional Patent Application No. 61/247,204 filed Sep. 30, 2009, the disclosure of which is incorporated herein by reference.

The subject of the present invention is a composition containing Arabinogalactan for enhancing the adaptive immune response in subjects by administering said composition prior, during and after the phase of exposure to a foreign antigen. Furthermore, the present invention relates to a vaccination kit comprising a composition containing Arabinogalactan and a vaccine.

BACKGROUND OF THE INVENTION

The immune system is a highly complex orchestration of several sub-systems which protect the host against infectious agents and cancerous cells. The immune system performs surveillance and must appropriately attack pathogens; it must also be able to recognize and spare cells which belong to the host. Immunomodulation is the ability of the hormones and other molecules to selectively alter the sensitivity of the immune system to mount attacks in response to antigenic stimulation. This is preferred to overstimulation (or hypersensitivity) of the immune system which may lead to damage to the host cells. The immune system consists of two major parts, namely the innate arm and the adaptive arm.

Said adaptive arm rests on the intricate interplay of various types of immune cells like dendritic cells, T-cells and B-cells as well as a wide range of immunomodulatory substances like cytokines to mount a successful production of antibodies. However, if the immune system encounters a foreign antigen for the first time, its reaction is frequently too slow/too weak to stop the initial spread of said antigen. Thus, there is a need to keep the immune system in a "primed" or heightened state of alert prior to the first encounter of a foreign antigen.

Furthermore, there is a need to enhance an on-going immune response in order to have the immune system clear the foreign antigen from the body as quickly as possible.

In order to help the immune system ward off potentially harmful invaders, a method of artificial induction of an immune response called "vaccination" was systematically employed for the first time in the 18$^{th}$ century. Vaccination is the administration of antigenic material (the vaccine) to produce immunity to a disease. Vaccines can prevent or ameliorate the effects of infection by a pathogen. Vaccination is generally considered to be the most effective and cost-effective method of preventing infectious diseases. The material administered can either be live but weakened forms of pathogens (bacteria or viruses), killed or inactivated forms of these pathogens, or purified material such as proteins.

However, a vaccination with the antigenic material alone frequently fails to provoke an immune response that is sufficiently strong to convey complete or even partial immunity. Thus, adjuvants are used to boost the immune response. Broadly speaking, adjuvants fall into two classes: inorganic and organic adjuvants.

Typical examples of inorganic adjuvants are aluminium salts, e.g. aluminium phosphate and aluminium hydroxide. Due to their low to non-existent toxicity, they are the most widely used adjuvants in human vaccinations.

Organic adjuvants are usually selected from components of the bacterial cell wall like lipopolysaccharide (LPS) and from endocytosed nucleic acids such as double-stranded RNA (dsRNA), single-stranded DNA (ssDNA), and unmethylated CpG dinucleotide-containing DNA. The reason for this is that immune systems have evolved to recognize and react against these specific antigenic moieties.

Thus, there is a need for additional adjuvants that help boost an immune response while at the same time being non-toxic and that do not induce any severe side effects in subjects.

Larch Arabinogalactan is a highly branched polysaccharide that is composed of galactose units and arabinose units in the approximate ratio of 6:1. It is a fine, dry, light brown powder with neutral taste and, in case it is extracted from larch trees, a mild pine-like odour. It dissolves quickly in water or juice.

Studies on improvement of response to a pneumococcal vaccine by adults include revaccination, the addition on conjugates to the vaccine and alternative antigenic substances.[1] Experiments have also been conducted on the use of supplements, including zinc, vitamin A and L-arginine to increase the response to the vaccine.[2,3] Some plants are known to contain substances that modulate the immune system. As an example, an extract of the plant *Uncana tomentosa* was reported to enhance the response to a pneumococcal vaccine in male volunteers, elevating lymphocyte/neutrophil ratios and increasing the persistence of the antibody response to the vaccine.[4]

Several immune-enhancing herbs, including *Echinacea purpurea, Baptista tinctoria, Thuja occidentalis, Angelica acutiloba*, and *Curucuma longa* and the medicinal mushroom *Ganoderma lucidum* contain compounds known as Arabinogalactans.[5] Larch arabinogalactan has demonstrated immunomodulating activity in vitro and in vivo.[6,7]. However, said immunomodulating effect was thus far limited to the innate arm of the immune system. Nothing in the state of the art indicates that Larch Arabinogalactan is capable of modulating the adaptive arm of the immune system.

DISCLOSURE OF THE INVENTION

The technical problems laid out above are surprisingly solved by using a composition containing Arabinogalactan for enhancing the adaptive immune response in subjects as defined in the claims.

Specifically, the present invention discloses a composition containing Arabinogalactan for enhancing the adaptive immune response against foreign antigen(s), whereby said composition is administered to the subjects prior, during and after the phase of exposure to said antigen(s).

"Subjects" according to the invention are vertebrates, preferably mammals and birds, more preferably swine, poultry, beef cattle, dogs, cats, goats and horses, most preferably humans.

"Antigen" according to the invention relates to any substance capable of being recognized by the adaptive arm of the immune system. Preferably, the antigen is either an exogenous or endogenous antigen, while autoantigens are excluded. Preferably, the antigen according to the invention is derived from a pathogen, preferably a virus or a bacterium.

A "virus" according to the invention is a member of one of the five orders as defined by the ICTV classification, i.e. *Caudovirales, Herpesvirales, Mononegavirales, Ndovirales*, and *Picornavirales* or a member of one of the seven Groups of the Baltimore classification, i.e. dsDNA viruses, ssDNA viruses, dsRNA viruses, (+)ssRNA viruses, (−)ssRNA viruses, ssRNA-RT viruses, dsRNA-RT viruses. Preferably, the virus according to the invention is a member of the family of Orthomyxoviridae, more preferably a member of the genera Influenzavirus A-C, even more preferably of the species Influenza A, Influenza B or Influenza C virus and most preferably of the serotype H1N1, H1N2, H2N2, H3N1, H3N2, H3N8, H5N1, H5N2, H5N3, H5N8, H5N9, H7N1, H7N2, H7N3, H7N4, H7N7, H9N2 or H10N7.

A "bacterium" according to the invention generally refers to a prokaryotic member of the domain Bacteriae. More preferably, a bacterium according to the invention belongs to one of the currently known phyla, i.e. Actinobacteria, Aquificae, Bacteriodetes/Chlorobi, Chlamydiae/Verrucomicrobia, Chloroflexi, Chrysiogenetes, Cyanobacteria, Deferribacteres, Deinococcus-Thermus, Dictyoglomi, Fibrobacteres/Acidobacteria, Firmicutes, Fusobacteria, Gemmatimonadetes, Nitrospirae, Planctomycetes, Proteobacteria, Spirochaetes, Synergistetes, Tenericutes, Thermodesuflobacteria and Thermotogae.

Even more preferably, the bacterium according to the invention belongs to the genus *Streptococcus, Staphylococcus, Chlamydia, Mycobacterium, Clostridium, Salmonella, Haemophilus, Legionella, Campylobacter, Bacillus, Escherichia, Enterococcus, Klebsiella, Lactobacillus* or *Pseudomonas*.

Most preferably, the bacterium according to the invention is the strain *Streptococcus pneumoniae*.

Other antigens according to the invention include toxins, prions, viroids and satellites.

"Arabinogalactan" according to the invention is to be understood as relating to any compound that is composed of galactose units and arabinose units in the approximate ratio of 100:1 to 1:1, preferably 6:1, Specifically, Arabinogalactan according to the invention is preferably characterized by having a backbone of (1→3)-linked β-D-galactopyranosyl units, each of which bears a substituent at the C-6 position. Most of these side chains are galactobiosyl units containing a (1→6)-β-D-linkage as well as α-L-arabinofuranosyl units. However, the scope of the present invention also encompasses Arabinogalactan derivatives, e.g. where Arabinogalactan is in covalent association with varying amounts of protein (Arabinogalactan-proteins (AGPs) as described in Classen et al., "*Characterization of an Arabinogalactan-protein isolated from pressed juice of Echinacea purpurea by precipitation with the β-glucosyl Yariv reagent*", Carbohydrate Research, 327 (2000), 497-504). Other derivatives include quaternized or lipidated forms of Arabinogalactan.

According to the invention, it may be preferred that the Arabinogalactan is derived from plants, namely dicotyledons and monocotyledons, with dicotyledons being preferred. It may further be preferred that the Arabinogalactan according to the invention is derived from pinophyta, more preferably pinaceae. It may be most preferred that the Arabinogalactan according to the invention is derived from Larch trees (*Larix* spp.), especially *Larix laricina*. "Composition" according to the invention relates to any composition that includes Arabinogalactan as defined above in an amount of 0.5 mg-30 g, preferably in an amount of 0.5 g-15 g and most preferably in an amount of 1.0-4.5 g.

Preferably, the composition containing Arabinogalactan is administered 70 days before the phase of exposure to foreign antigen(s), more preferably 50 days and most preferably 30 days.

It may be preferred that the composition containing Arabinogalactan is administered until 92 days, more preferably until 72 days and most preferably until 42 days after the phase of exposure to foreign antigen(s).

The composition containing Arabinogalactan may be administered in liquid or solid form. Preferably the Arabinogalactan is administered in the form of functional beverages, functional foods such as bars, breakfast cereals etc or as dietary supplements such as capsules, tablets, dry powder blends or premixes.

Preferably, the composition containing Arabinogalactan is administered to the subject on a daily basis. However, it may also be preferred that the composition containing Arabinogalactan is administered in longer or shorter intervals.

Generally, the composition containing Arabinogalactan may be used in conjunction with any vaccine. However, it may be preferred that the vaccine according to the invention is directed against an antigen derived from or being part of an agent selected from the group consisting of bacteria, viruses, toxins, prions, viroids and satellites. Said agent may also be used as a whole in the vaccination in either live or inactivated form.

It may be preferred that the vaccine is a pneumococcal vaccine. It may further be preferred that the vaccine is directed against bacteria from the genus *Streptococcus, Staphylococcus, Chlamydia, Mycobacterium, Clostridium, Salmonella, Haemophilus, Legionella, Campylobacter* or *Pseudomonas*., especially the strain *Streptococcus pneumoniae*.

The vaccination procedure can be carried out using any methodology known in the state of the art. Specifically, said vaccination procedure may be carried out subcutaneously, intramuscular, orally, nasally, by inhalation or via patches.

It may also be preferred that the vaccination procedure is carried out repeatedly to enhance the immune response.

Another aspect of the present invention concerns a kit comprising a vaccine and a composition containing Arabinogalactan. Said kit may be used to enhance the adaptive immune response upon vaccination.

The invention will be further described in the following, non-limiting examples.

EXAMPLES

Example 1

Investigational Products

The Resistaid™ product contains arabinogalactan extracted from Larch trees (*Larix* spp., mostly *Larix laricina*). Arabinogalactan is a highly branched polysaccharide that is composed of galactose units and arabinose units in the approximate ratio of 6:1. Resistaid™ is a fine, dry, light brown powder with neutral taste and a mild pine-like odor. It dissolves quickly in water or juice. Resistaid™ is produced via a water extraction patented process (U.S. Pat. No. 5,756, 098; EP 86608). The Larch arabinogalactan used in the Resistaid™ product has been Affirmed GRAS by the FDA (GRN000084).

The placebo was maltodextrin (Maltin M100). The test product and the placebo were administered by mixing the powders into a beverage of the subject's choice for a maximum period of 72 days. The subjects were advised to take their dosage (4.5 g) once a day in the morning with breakfast. First intake of the study medication was on Day 1.

Subjects

Subjects between the ages of 18 and 65 were recruited for the study in the usual manner (subject database and community advertisements). Subjects were phone-screened prior to scheduling a screening visit.

Subjects were included if they were 18-65 years of age, had a Body Mass Index (BMI)>18 kg/m2 and <30 kg/m2 at screening, agreed to all study visits and visit procedures, agreed to use approved forms of birth control, and agreed not to initiate/change any exercise or diet programs during the study. Subjects were excluded if they had previously had the pneumococcal vaccine, had allergies to the test product, had any major systemic, inflammatory or chronic disease, had any active infection or infection in the past month requiring antibiotics or anti-viral medication, used immunosuppressive drugs in the prior 5 years, were known to have alcohol or drug abuse, were pregnant or lactating or had any medical condition which in the opinion of the investigator might interfere with the subject's participation in the trial.

Study Design

The study was a randomized, double-blind, placebo-controlled, parallel group trial with an active investigational period of 72 days. The primary objective was to assess the immunomodulatory effect of Resistaid™ on selective markers of immune function in the face of antigenic challenge by the pneumococcal pneumonia vaccine. The primary endpoints included 7 different pneumococcal IgG antibodies. The secondary objective was determine whether the Resistaid™ product would stimulate other arms of the immune system to which there was no direct antigenic stimulus. Secondary endpoints included salivary IgA, white blood cell counts, complement (C3 and C4) and inflammatory cytokine levels. The study was conducted at the Medicus Research clinical research site located in Northridge, Calif. IRB approval was obtained prior to the initiation of any study activities (Copernicus Group IRB, Cary, N.C.).

Subjects meeting the inclusion/exclusion criteria for this study were assigned to group using randomized block design. Double-blinding was ensured by identical sachets, outer package, labelling, color, and consistency of both investigational products (investigational study product and placebo). Unblinding of the entire research team, including data analysis team did not occur until after the analysis was completed; subjects were blinded throughout the trial.

The subjects in the study came to the research clinic for a total of 5 visits (V1-V5) over 72 days. Subjects took the first dose of assigned study product at the screening visit (V1-Day 0) and continued to take them over the entire study. They received the 23-valent pneumococcal vaccine at the baseline visit which took place 30 days after they began taking the product or placebo (V2-Day 30). They came in for safety monitoring the day immediately following the vaccine (V3-Day 31) to observe the reaction at the vaccine administration site. Then subjects returned 21 days after vaccine (V4-Day 51) and finally 42 days after vaccine administration (V5-Day 72). On study visits, blood, urine and saliva were collected and subjects were queried regarding any change in health status. Additionally, they were assessed for compliance by interview, diary, and through assessment of returned study product bottles.

The most potentially immunogenic pneumococcal antibodies (Ab) were determined in consultation the UCLA Vaccine Center as the antibodies most likely to respond to vaccination with the commercially available 23-valent pneumococcal vaccine. These antibodies included 4, 6B, 9V, 14, 18C, 19F, and 23F. Salivary IgA was measured to monitor for non-specific effects on the adaptive immune system.

Other markers of immune function were chosen to represent the innate arm of the immune system including white blood cell counts (totals and subtypes), inflammatory cytokines, and complement (C3 and C4). Safety monitoring included: body temperature, blood pressure, heart rate, physical exam, urinalysis, complete blood counts (CBC) and a comprehensive metabolic panel (CMP) including kidney and liver function tests.

Analyses

Excel 2003 (Microsoft Corp, Redmond Wash.), was used for data entry, validation, restructuring, calculating changes in variables over time, reorganizing and reformatting results, and preparing graphs. Statistical analyses were performed using SPSS Base System ver. 17 (SPSS Inc., Chicago Ill.).

Data was analyzed using paired sample t-tests for within subject means comparisons, independent sample t-tests for between group comparisons (Placebo vs. the active groups individually). Difference scores for both within and between group comparisons (Placebo vs. the active groups individually) were analyzed using appropriate t-tests. Analysis was completed before the blinding code was broken.

Results

Subjects

Sixty five (65) subjects were screened in person at the research clinic and 53 qualified for randomization at the screening visit (V1). Of the 53, 8 did not return for V2 and therefore a total of 45 subjects were included in the intent-to-treat analysis. The subject baseline characteristics are given in Table 1. There were no significant differences between groups at baseline and there were no significant changes in body weight during the study in either group.

TABLE 1

Subject Demographics

|  | Resistaid(TM) | Placebo |
|---|---|---|
| N | 21 | 24 |
| Male | 6 (42.9%) | 16 (66.7%) |
| Female | 12 (57.1%) | 8 (33.3%) |
| Age (range) | 33.52 (19-62) | 38.25 (20-64) |

Pneumococcal IgG Antibodies

Pneumococcal IgG antibody subtypes 4, 6B, 9V, 14, 18C, 19F, and 23F were measured on Days 0 (V1), 51 (V4), and 72 (V5). There were no significant differences between the groups at baseline (Day 0).

Pneumococcal IgG levels increased from baseline as expected in response to the vaccine. Supplementation with Resistaid™ caused a significantly greater increase from baseline in pneumococcal IgG antibody subtypes 18C and 23F at both 51 and 72 days (Table 2). Mean values between groups were also significantly greater in the Resistaid group for both days 51 and 72 for these two subtypes (Table 3).

Change scores from baseline and mean values were greater in the Resistaid group than placebo for most timepoints in Ab subtypes 4, 6B, 9V, and 19F, but these differences did not reach statistical significance.

TABLE 2

Comparisons in mean values for
*Pneumococcal* Subtypes 18C and 23F

| | | | 18C Abs | | | |
|---|---|---|---|---|---|---|
| Day 0 | Resistaid | 21 | 1.4905 | 2.97891 | .65005 | .061 |
| (Screen) | Placebo | 24 | .7167 | 1.34993 | .27555 | |
| Day 51 | Resistaid | 21 | 9.5667 | 7.96438 | 1.73797 | .006 |
| | Placebo | 24 | 5.0583 | 5.80157 | 1.18424 | |
| Day 72 | Resistaid | 21 | 9.1048 | 7.53196 | 1.64361 | .008 |

TABLE 2-continued

Comparisons in mean values for
Pneumococcal Subtypes 18C and 23F

|  |  |  |  |  |  |  |
|---|---|---|---|---|---|---|
|  | Placebo | 24 | 4.9333 | 5.26338 | 1.07438 |  |
|  |  |  | 23F Abs |  |  |  |
| Day 0 | Resistaid | 21 | .7429 | .92605 | .20208 | .059 |
| (Screen) | Placebo | 24 | 1.0833 | 1.87516 | .38277 |  |
| Day 51 | Resistaid | 21 | 7.0714 | 7.40602 | 1.61613 | .002 |
|  | Placebo | 24 | 4.3250 | 4.62011 | .94308 |  |
| Day 72 | Resistaid | 21 | 7.0238 | 7.31505 | 1.59627 | .041 |
|  | Placebo | 24 | 4.5458 | 5.23084 | 1.06774 |  |

TABLE 3

Comparisons in change from baseline values
for Pneumococcal Subtypes 18C and 23F

|  |  |  |  |  |  |  |
|---|---|---|---|---|---|---|
|  |  |  | 18c |  |  |  |
| Day 51 to Day 0 | Resistaid | 21 | 8.0762 | 7.12481 | 1.55476 | .033 |
| (Screen) Change | Placebo | 24 | 4.3417 | 5.09645 | 1.04031 |  |
| Day 72 to Day 0 | Resistaid | 21 | 7.6143 | 6.80605 | 1.48520 | .012 |
| (Screen) Change | Placebo | 24 | 4.2167 | 4.63270 | .95789 |  |
|  |  |  | 23F |  |  |  |
| Day 51 to Day 0 | Resistaid | 21 | 6.3286 | 7.36180 | 160643 | .001 |
| (Screen) Change | Placebo | 24 | 3.2417 | 4.28251 | .87416 |  |
| Day 72 to Day 0 | Resistaid | 21 | 6.2810 | 7.16782 | 1.56415 | .003 |
| (Screen) Change | Placebo | 24 | 3.4625 | 4.23985 | .86546 |  |

Salivary IgA

There were no significant changes increases in salivary IgA from Day 0 to Days 51 or Day 0 to Day 72 in either group. There were also no significant differences in the mean values between groups.

White Blood Cells

Comparisons between the Arabinogalactan and Placebo groups on Days 0, 30, 31, 51 or 72 found no significant differences in white blood cell counts. The change from baseline Day 0 to Day 72 was significantly greater in the Arabinogalactan group than the Placebo group (p=0.045), however the magnitude of the change scores were too small to be clinically significant.

There were no significant differences in lymphocyte, neutrophil, monocyte, or basophil counts when comparing mean values between groups at any timepoint. When comparing change from baseline at each timepoint, there were no difference between groups for lymphocytes, neutrophils, or monocytes. Change from baseline comparisons for basophils were not different except for the change from Day 0 to Day 72 in which there was a small but significant difference in favor of the placebo group (p=0.042).

Eosinophil counts were different between groups at Day 30 (p=0.006) and Day 51 (p=0.014) in favor of the Arabinogalactan group. The change from baseline to Day 31 and the change from baseline to Day 51 were also significant in favor of the Arabinogalactan group (p=0.035 and p=0.006 respectively).

Complement

Comparisons of means and changes from baseline for complement levels between the Arabinogalactan and Placebo groups were not significantly different.

Cytokines

Analysis of inflammatory cytokine levels was performed using sandwich immunoassay (Affymetrix, San Diego, Calif.). Comparison of cytokine levels between groups found no significant differences in means for epithelial neutrophil-activating peptide (ENA)-78, eotaxin, granulocyte monocyte colony stimulating factor (GM-CSF), interferon-gamma (IFNg), interleukin (IL)-10, IL-12P40, IL-1RA, IL-2, IL-4, IL-5, IL-6, IL-8, monocyte chemotactic protein (MCP)-1, MCP-3, platelet-derived growth factor (PDGF)-BB or tumor necrosis factor (TNF)-alpha. When comparing the cytokine change from baseline values between groups, only the IL-6 change from Day 0 to Day 31 showed a significant difference in favor of the Arabinogalactan group (p=0.046).

Safety

No serious adverse events were reported during this study. There were nine mild to moderate adverse events: two in the Arabinogalactan group and seven in the Placebo group. The adverse events were determined to be unrelated to study product and were exacerbations of pre-existing medical conditions. All AE's were followed by the medical staff at the research clinic.

LITERATURE

1. Artz A S, Ershler W B, Longo D L: Pneumococcal vaccination and revaccination of older adults. Clin Microbiol Rev 2003, 16: 308-318.
2. Deloria-Knoll M, Steinhoff M, Semba R D, Nelson K, Vlahov D, Meinert C L: Effect of zinc and vitamin A supplementation on antibody responses to a pneumococcal conjugate vaccine in HIV-positive injection drug users: a randomized trial. Vaccine 2006, 24: 1670-1679.
3. Moriguti J C, Ferriolli E, Donadi E A, Marchini J S: Effects of arginine supplementation on the humoral and innate immune response of older people. Eur J Clin Nutr 2005, 59: 1362-1366.
4. Lamm S, Sheng Y, Pero R W: Persistent response to pneumococcal vaccine in individuals supplemented with a novel water soluble extract of Uncaria tomentosa, C-Med-100. Phytomedicine 2001, 8: 267-274.
5. Roxas M, Jurenka J: Colds and influenza: a review of diagnosis and conventional, botanical, and nutritional considerations. Altern Med Rev 2007, 12: 25-48.
6. Kelly G S: Larch arabinogalactan: clinical relevance of a novel immune-enhancing polysaccharide. Altern Med Rev 1999, 4: 96-103.
7. Currier N L, Lejtenyi D, Miller S C: Effect over time of in-vivo administration of the polysaccharide arabinogalactan on immune and hemopoietic cell lineages in murine spleen and bone marrow. Phytomedicine 2003, 10: 145-153.

The invention claimed is:

1. A kit comprising a composition consisting essentially of:
1) the polysaccharide Arabinogalactan and/or at least one Arabinogalactan derivative, and 2) a vaccine, wherein said Arabinogalactan derivative is selected from the group consisting of Arabinogalactan proteins and quaternized forms of Arabinogalactan.

2. The kit according to claim 1, whereby said vaccine is a pneumococcal vaccine.

3. The kit according to claim 1, wherein said Arabinogalactan is derived from plants.

4. The kit according to claim 2, whereby said pneumococcal vaccine is directed against bacteria from the strain *Streptococcus pneumoniae*.

5. A method for enhancing the adaptive immune response against foreign antigen(s), the method comprising administration of a composition consisting essentially of: 1) the polysaccharide Arabinogalactan and/or at least one Arabinogalactan derivative, and 2) a vaccine, wherein said Arabinogalactan derivative is selected from the group consisting of Arabinogalactan proteins and quaternized forms of Arabinogalactan.

* * * * *